United States Patent
Schuster et al.

(10) Patent No.: US 12,365,507 B2
(45) Date of Patent: Jul. 22, 2025

(54) PACK AND METHOD FOR FILLING A PACK

(71) Applicant: Uhlmann Pac-Systeme GmbH & Co. KG, Laupheim (DE)

(72) Inventors: Jochen Schuster, Laupheim (DE); Matthias Konrad, Laupheim (DE)

(73) Assignee: UHLMANN PAC-SYSTEME GMBH & CO. KG, Laupheim (DE)

( * ) Notice: Subject to any disclaimer, the term of this patent is extended or adjusted under 35 U.S.C. 154(b) by 16 days.

(21) Appl. No.: 18/423,962

(22) Filed: Jan. 26, 2024

(65) Prior Publication Data

US 2024/0253850 A1    Aug. 1, 2024

(30) Foreign Application Priority Data

Jan. 27, 2023    (EP) ..................... 23153694

(51) Int. Cl.
 *B65D 5/50*    (2006.01)
 *B65D 5/02*    (2006.01)
 (Continued)

(52) U.S. Cl.
 CPC ......... *B65D 5/5016* (2013.01); *B65D 5/0254* (2013.01); *B65D 85/42* (2013.01); *A61M 5/002* (2013.01)

(58) Field of Classification Search
 CPC .... B65D 5/5016; B65D 5/0254; B65D 5/068; B65D 5/5038; B65D 5/20; B65D 5/5059;
 (Continued)

(56) References Cited

U.S. PATENT DOCUMENTS 2,084,540 A * 6/1937 Smith ................... B65D 5/5038
 206/365
2,473,582 A * 6/1949 Goodwin ............. B65D 5/5038
 206/583
(Continued)

FOREIGN PATENT DOCUMENTS

CN    111232356 A    6/2020
DE    4024112 A1    2/1992
(Continued)

OTHER PUBLICATIONS

Chris H: "DPP260T1 XWZ120 Horizontal Injection Blister Cartoner Production Line", Jul. 11, 2017, XP93075694, Gefunden im Internet: URL:https://www.youtube.com/watch?v=ryNitVbxzYA&ab_channel=ChrisH [gerfunden am Aug. 23, 2023].
(Continued)

*Primary Examiner* — Ernesto A Grano
(74) *Attorney, Agent, or Firm* — Dickinson Wright PLLC

(57) ABSTRACT

The pack for products has a bottom layer, an intermediate layer, and a top layer, which are arranged one above the other and at a distance from one another and which are connected to each other. The top layer has a receiving strip, which has a plurality of recesses. The receiving strip is pivotable in the direction of the bottom layer about a pivoting axis, which is arranged in the region of the top layer. In the pivoted receiving state of the receiving strip, entry openings of the recesses for the insertion of the products point away from the bottom layer, and supporting sections of the recesses for supporting portions of the products form a boundary of the recesses which lies opposite the entry openings. The intermediate layer has an aperture in a pivoting range of the receiving strip.

11 Claims, 6 Drawing Sheets

(51) Int. Cl.
*B65D 85/42* (2006.01)
*A61M 5/00* (2006.01)

(58) Field of Classification Search
CPC ...... B65D 81/025; B65D 85/42; B65D 71/72;
B65B 23/22; A61M 5/002
USPC ........................................................ 206/571
See application file for complete search history.

(56) References Cited

U.S. PATENT DOCUMENTS

| | | | | |
|---|---|---|---|---|
| 2,593,430 A * | 4/1952 | Frankenstein | ....... | B65D 5/5038 |
| | | | | 206/217 |
| 2,833,457 A * | 5/1958 | Tyrseck | ................ | B65D 5/524 |
| | | | | 229/164 |
| 3,292,777 A * | 12/1966 | Desmond | ............ | B65D 5/5009 |
| | | | | 206/783 |
| 3,351,182 A * | 11/1967 | Greer | ........................ | B65D 5/52 |
| | | | | 206/758 |
| 4,274,579 A * | 6/1981 | Kulig | .................... | B65D 71/72 |
| | | | | 229/120.08 |
| 4,278,197 A * | 7/1981 | Scheinbaum | .......... | B65D 71/72 |
| | | | | 206/217 |
| 4,697,707 A * | 10/1987 | Engdahl | ............... | B65D 5/5038 |
| | | | | 426/106 |
| 4,905,820 A * | 3/1990 | Hart | ..................... | B65D 5/5016 |
| | | | | 206/783 |
| 5,330,052 A * | 7/1994 | Van Hest | ............. | B65D 5/0209 |
| | | | | 206/419 |
| 5,871,145 A * | 2/1999 | Hermann | ............. | B65D 5/5016 |
| | | | | 206/443 |
| 6,168,012 B1 * | 1/2001 | Galbierz | ................ | B65D 71/46 |
| | | | | 206/153 |
| 6,935,505 B1 * | 8/2005 | Nash, Jr. | ................ | B65D 71/72 |
| | | | | 206/486 |
| 8,925,723 B2 * | 1/2015 | Folchini | ............... | B65D 5/5007 |
| | | | | 206/370 |
| 11,420,786 B1 * | 8/2022 | Ansola, III | ............ | B65D 71/72 |
| 11,738,926 B2 * | 8/2023 | Ansola, III | .......... | B65D 71/004 |
| | | | | 206/427 |
| 2006/0158733 A1 * | 7/2006 | Billen | .................. | B65D 5/5007 |
| | | | | 359/474 |
| 2006/0278559 A1 * | 12/2006 | Hamblin | ................ | B65D 71/72 |
| | | | | 206/562 |
| 2007/0158234 A1 * | 7/2007 | Sakai | .................... | B65D 5/0254 |
| | | | | 206/784 |
| 2010/0276306 A1 * | 11/2010 | Specker | ................. | B65D 5/504 |
| | | | | 206/193 |
| 2013/0062245 A1 * | 3/2013 | Folchini | ................ | A61M 5/002 |
| | | | | 493/162 |
| 2014/0124395 A1 * | 5/2014 | Nadeau | ................ | B65D 5/5038 |
| | | | | 206/250 |
| 2019/0177031 A1 * | 6/2019 | Vanderwell | .......... | B65D 5/5038 |
| 2020/0039681 A1 * | 2/2020 | Monti | .................. | B65D 5/3621 |
| 2022/0008645 A1 * | 1/2022 | Ukai | ................... | A61M 5/3129 |
| 2022/0024666 A1 * | 1/2022 | Creager | .................... | B65D 5/52 |
| 2022/0089312 A1 * | 3/2022 | Meuti | ................... | B65D 5/504 |
| 2022/0267045 A1 * | 8/2022 | Sasso | ................... | B65D 5/5038 |
| 2023/0140636 A1 * | 5/2023 | Autajon | ................ | B65D 5/0254 |
| | | | | 206/526 |
| 2023/0159244 A1 * | 5/2023 | Ansola, III | ............ | B65D 71/72 |
| | | | | 206/427 |
| 2023/0356878 A1 * | 11/2023 | Cobert | ................ | B65D 5/5007 |
| 2024/0166404 A1 * | 5/2024 | Henigman | ........... | B65D 65/403 |
| 2025/0019115 A1 * | 1/2025 | Heinen | .................. | A61C 19/02 |
| 2025/0033865 A1 * | 1/2025 | Bressan | ................. | B65D 5/503 |

FOREIGN PATENT DOCUMENTS

DE 102018203788 A1 9/2019
FR 1438108 A 5/1966

OTHER PUBLICATIONS

European Search Report from European Application No. 23153694.7-1014 dated Sep. 1, 2023.

* cited by examiner

PACK AND METHOD FOR FILLING A PACK

CROSS-REFERENCE TO RELATED APPLICATIONS

This application claims the benefit of and priority under 35 U.S.C. § 119 to European Patent Application No. 23 153 694.7, filed Jan. 27, 2023, the contents of which is incorporated herein by reference in its entirety.

FIELD

The present disclosure relates to a pack and to a method for filling a pack.

BACKGROUND

Packs, especially those made of cardboard, e.g. in the form of trays, are used in many sectors of industry for packaging products. Among examples of such products are products for liquids in the pharmaceutical industry, especially syringes, ampoules or vials.

SUMMARY

The present disclosure provides a pack which is particularly stable and in which the products are stored particularly safely.

According to an aspect of the disclosure, the pack, in particular a tray, for products comprises a bottom layer and a top layer, which are arranged one above the other and at a distance from one another and which are connected to one another. The top layer has at least one receiving strip, preferably a plurality of receiving strips, wherein each receiving strip has a plurality of recesses, wherein the at least one receiving strip is pivotable in the direction of the bottom layer about at least one pivoting axis, which is arranged in the region of the top layer. In the pivoted receiving state of the at least one receiving strip, entry openings of the recesses for the insertion of the products point away from the bottom layer, and supporting sections of the recesses for supporting portions of the products form a boundary of the recesses which lies opposite the entry openings.

As a result, the pack as a whole is stable, and the products can be fed into the pack in a simple manner and rest securely in the respective recesses.

The pack further has an intermediate layer, which is arranged between the bottom layer and the top layer, at a distance from the bottom layer and the top layer, and is connected to the bottom layer and/or to the top layer, wherein the intermediate layer has at least one aperture in the pivoting range of the at least one receiving strip. The stability of the pack is thereby increased even further.

There is a general preference for all three layers, i.e. the bottom layer, intermediate layer and top layer, to be connected, preferably firmly connected, to one another directly or indirectly.

The pack can be used for many types of products consisting of solid bodies. It is particularly suitable especially for products which have an extent in a main direction of extent (longitudinal direction) of at least 20 mm, preferably at least 30 mm, more preferably at least 40 mm. One specific application is for products for the pharmaceutical industry, especially syringes, ampoules and/or vials.

It is preferred that the at least one aperture in the intermediate layer has at least one edge contour, against which the downwardly pivoted receiving strip abuts. In this way, the pivoted receiving strip is additionally stabilized.

In a preferred embodiment, the at least one edge contour is a convex contour or has mutually spaced sections which, when connected virtually, define a convex contour. As a result, the receiving strip is pre-stressed, further contributing to stabilization.

The height of the convex contour at the vertex thereof, measured from the line of intersection through the two end points of the convex contour, is preferably between 1 and 10 mm, more preferably between 3 and 5 mm.

Alternatively or in addition, the height of the convex contour at the vertex thereof, measured from the line of intersection through the two end points of the convex contour, is preferably between 1% and 20%, more preferably between 2 and 10%, of the width of the convex contour between the two end points. Such a small degree of convexity has proven optimal for stabilization.

Alternatively or in addition, the convex contour preferably has the shape of a circular segment with a radius of curvature of between 25 and 2500 mm, more preferably between 60 and 600 mm.

In a preferred embodiment, the intermediate layer has, in the at least one aperture and preferably close to the edge contour, at least one latching lug, preferably two symmetrically arranged latching lugs, for the downwardly pivoted receiving strip. The stability of the pack is thereby further increased because it would only be possible to pivot the receiving strip back over the latching lug with a considerable application of force.

In the unpivoted initial state, the at least one receiving strip and the recesses thereof preferably extend substantially flat with respect to the remaining main body of the top layer. Alternatively, they can also extend obliquely at an angle of no more than 30°, preferably no more than 20°, more preferably no more than 10°, relative to the main body of the top layer.

In the pivoted state, the plane in which a receiving strip lies preferably intersects the bottom layer at an angle of +/−65° to 90°, more preferably of +/−75° to 85°.

The pivoting axis of the receiving strip is preferably defined by at least one groove edge, preferably two symmetrically arranged groove edges, in the top layer. This simplifies the production of the pack while ensuring reliable functionality. However, other forms of hinge are also conceivable.

The receiving strip and the main body of the top layer are preferably each connected to one another in two opposite side regions of the top layer. In this way, reliable pivoting of the receiving strip about two fastening points is achieved.

In a preferred embodiment, the top layer has two receiving strips, which are pivotable in opposite directions and the recesses of which serve to receive different portions of the same products. This serves for simple automated pivoting and thus simple feeding of long products into the recesses.

The intermediate layer preferably has, offset from the receiving strips, supporting surfaces or supporting lines for supporting additional product portions and/or has apertures for receiving additional product portions.

As a particular preference, the pack is formed completely from cardboard. In particular, the top layer should be formed from cardboard. However, it is also conceivable to use other suitable materials or to use different materials for different elements of the pack.

It is also preferred that the entire pack should be formed from a single pack blank.

In general, it is preferred if the pack has a substantially cuboidal configuration. In this case, the height of the cuboid is preferably significantly smaller than the length of the cuboid, e.g. by at least a factor of 2 or a factor of 3. Moreover, the height of the cuboid is preferably significantly smaller than the width of the cuboid, e.g. by at least a factor of 1.5 or a factor of 2.

However, other basic shapes of the pack, preferably with at least six side faces, are also conceivable. The pack can also have a cube-shaped configuration, for example. Basic shapes with more than six side faces, e.g. eight or ten side faces, are likewise conceivable.

In principle, it is advantageous if side strips of the erected pack are connected, preferably firmly connected, particularly preferably adhesively bonded, to one another at least on one longitudinal side, preferably on two longitudinal sides, in order to form a body of the pack. Finally, closure tabs, the folding over of which after the filling of the pack ensures end closure and a particularly stable shape of the pack, are arranged at the two ends of the pack.

In the case of a pack which is produced from a single pack blank, the bottom layer can, for example, already be connected integrally via two connecting strips both to the top layer and to the intermediate layer on one side in each case. Two outer side strips of the pack blank, which were originally arranged on that side of the intermediate layer or top layer which faces away from the bottom layer in the flat state of the pack blank, are then used for connection, preferably adhesive bonding, to in each case one of the two connecting strips, which were originally arranged between the bottom layer and the intermediate layer or the bottom layer and the top layer in the flat state of the pack blank. In this way, a stable body shape of the pack is achieved.

In principle, however, it would also be conceivable to produce individual layers of the pack as separate elements and to connect them to one another only when assembling the pack.

The products rest in the recesses of the receiving strip and optionally on the supporting surfaces of the intermediate layer in addition. In general, the products rest on top in such a way that they can be grasped by the user without further opening measures, and are therefore preferably uncovered.

Overall, it is advantageous if, although the top layer comprises a multiplicity of webs and the at least one receiving strip, other large regions of the top layer exhibit apertures.

The pack is generally also inserted into a folding box and is then distributed in this form. In addition to those elements of the pack which have been described, however, an additional covering film may additionally be sealed onto the webs of the top layer of the pack. In such a case, the insertion of the pack into an additional surrounding folding box could possibly be omitted.

The recesses of the at least one receiving strip can have a shape which tapers in the direction of the entry openings, for example. This ensures that the products are reliably protected from falling out of the recesses. As the products are introduced, these tapers are then each bent open briefly by virtue of the elasticity of the material of the receiving strip.

The recesses of the at least one receiving strip generally accommodate only a small product portion. The extent of the recesses of the at least one receiving strip in a main direction of extent (longitudinal direction) of the products is generally no more than 5 mm, preferably no more than 3 mm, more preferably no more than 2 mm. The extent of the recesses of the at least one receiving strip perpendicularly to the main direction of extent of the products is generally no more than 100 mm, preferably no more than 50 mm, more preferably no more than 10 mm.

A shape of the recess which is particularly suitable for cylindrical product portions, such as those of syringes, ampoules and vials, is a substantially circular shape. The circle radius is then preferably no more than 100 mm, more preferably no more than 50 mm, particularly preferably no more than 10 mm.

In the receiving strip, the respective recesses are arranged adjacent to one another and spaced apart from one another. In general, all the recesses of a receiving strip lie in the same plane. If there are several receiving strips, all the recesses of all the receiving strips preferably lie in planes that run parallel to one another. This is the case particularly if different product portions of the same product are supported by two or more receiving strips, as may be the case with syringes, for example. In such cases, the pivoting axes of the various receiving strips are also usually arranged parallel to one another in each case. The various receiving strips thus rotate either in the same direction or in an opposite direction.

However, it is also conceivable for different receiving strips to have recesses that are aligned differently and/or to have pivoting axes which are oblique or else, in particular, perpendicular to one another.

A preferred method for filling the pack comprises the steps of:
providing a pack as described above;
pivoting the at least one receiving strip in the direction of the bottom layer,
simultaneously introducing a plurality of products into the recesses of the at least one pivoted receiving strip.

Filling is thereby achieved in a simple manner.

Pivoting the at least one receiving strip and introducing the plurality of products into the recesses preferably take place in an automated manner and in one operation.

Pivoting the at least one receiving strip and introducing the plurality of products into the recesses preferably take place by means of at least one linear movement of a filling device in the direction of the bottom layer. This serves to additionally simplify the mechanized filling process.

The filling device can hold the plurality of products firmly but releasably by means of suction devices or grippers, for example.

During the filling process, the filling device preferably first of all butts up against the at least one receiving strip by means of shoulders or projections, preferably in a region close to the pivoting axis, thereby initiating the pivoting process. As the linear movement of the filling device in the direction of the bottom layer continues, a front part of the filling device, together with the products, passes through the aperture in the main body of the top layer, which becomes fully accessible as the receiving strip pivots, and the pivoting process is continued as far as a pivoting angle with an absolute value of preferably 65° to 90°, more preferably 75° to 85°. The latter range has proven advantageous because a small distance between the shoulders or projections of the filling device and the pivoting axes should be maintained in order, for example, to allow for certain tolerances.

At the end of the pivoting process, the at least one receiving strip preferably butts up against the preferably convex edge contour of the associated aperture in the intermediate layer and is thereby slightly pre-stressed. The convex edge contour is a further boundary condition, which, at least in some section or sections, requires a pivoting angle with a smaller absolute value than 90° and can furthermore lead to a slight deviation of the pivoting angle in different sections of the receiving strip.

If there are latching lugs, these additionally hold the receiving strip firmly in the pivoted end position. In the case of a convex edge contour of the associated aperture in the intermediate layer, the latching lugs also assist the pre-stressing of the receiving strip by jamming on preferably two opposite sides.

The transfer of the products into the receptacles is preferably likewise accomplished by linear movement, in the direction of the bottom layer, of the filling device which holds the products. In reality, there does not need to be a sharp distinction between the pivoting process and the filling process; instead, they can take place with a partial overlap.

After the products have been introduced into the recesses, the engagement between the filling device and the products is cancelled, and the then empty filling device can be moved back out of the pack by a linear movement in a direction away from the bottom layer.

The process described represents just one preferred possibility for the filling of the pack. It is, of course, also possible to provide different devices for pivoting the at least one receiving strip and for introducing the products into the recesses and/or to carry out the pivoting process and the filling process at different times. It is, of course, also possible to carry out one or more or all of the steps manually. Each product would then be fed in individually.

Apart from the linear lowering movement of the filling device, it is also possible for other movements to take place, e.g. at least one further linear movement of the filling device in some other direction before the introduction of the products into the pack, or linear co-movement of the filling device in the transport direction of the pack during the filling process in the case of continuous conveyance of the pack during the filling process.

DETAILED DESCRIPTION

Figure 1:
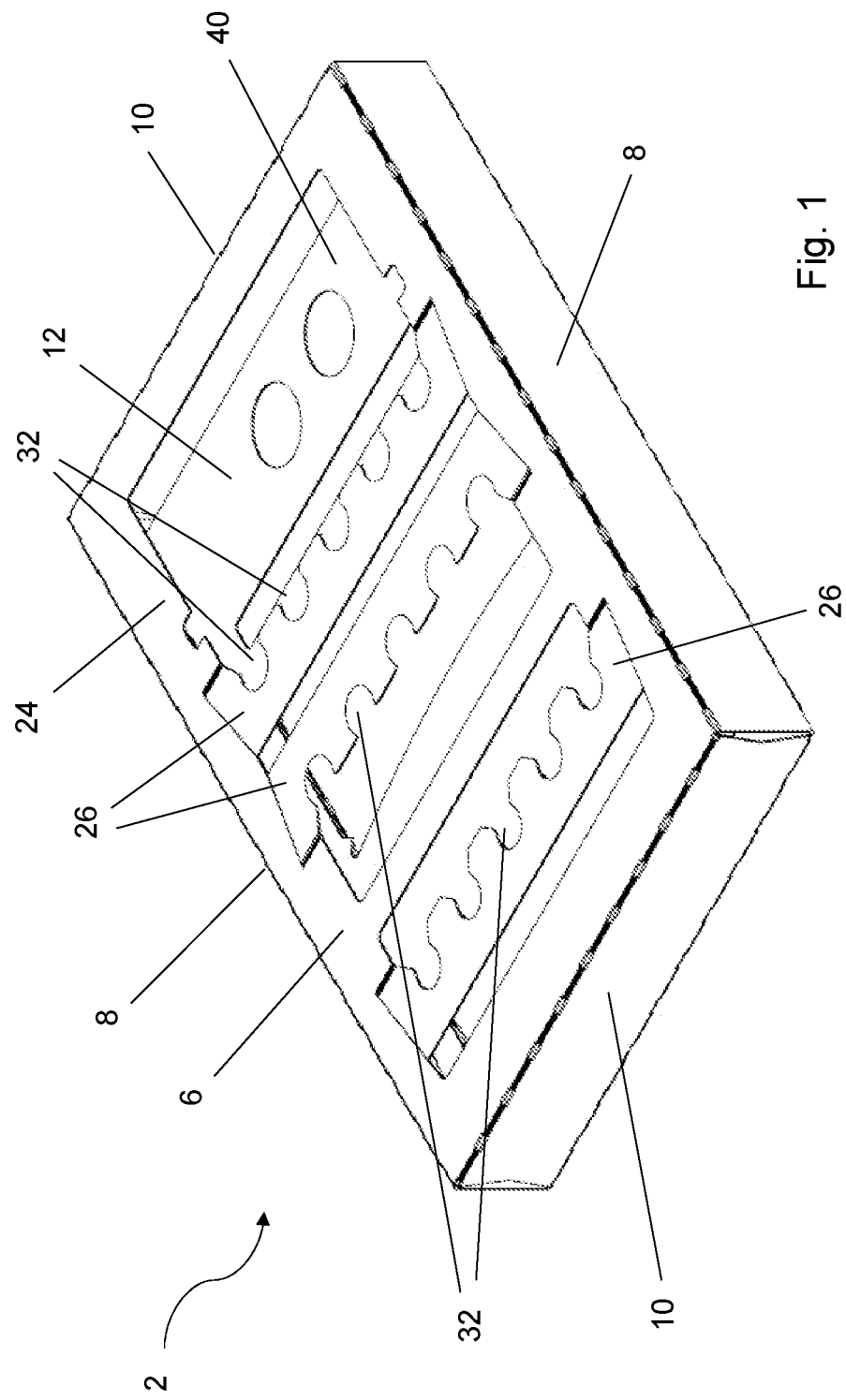
FIG. 1 is a perspective view of one embodiment of the pack according to the disclosure in an initial state with the receiving strips unpivoted.

FIG. 1 illustrates one embodiment of the pack 2 according to the disclosure in the initial state.

The pack 2 has substantially the shape of a cuboid with a bottom layer 4, a top layer 6, between which two mutually opposite longitudinal sides 8 and two mutually opposite ends 10 extend.

Figure 2:
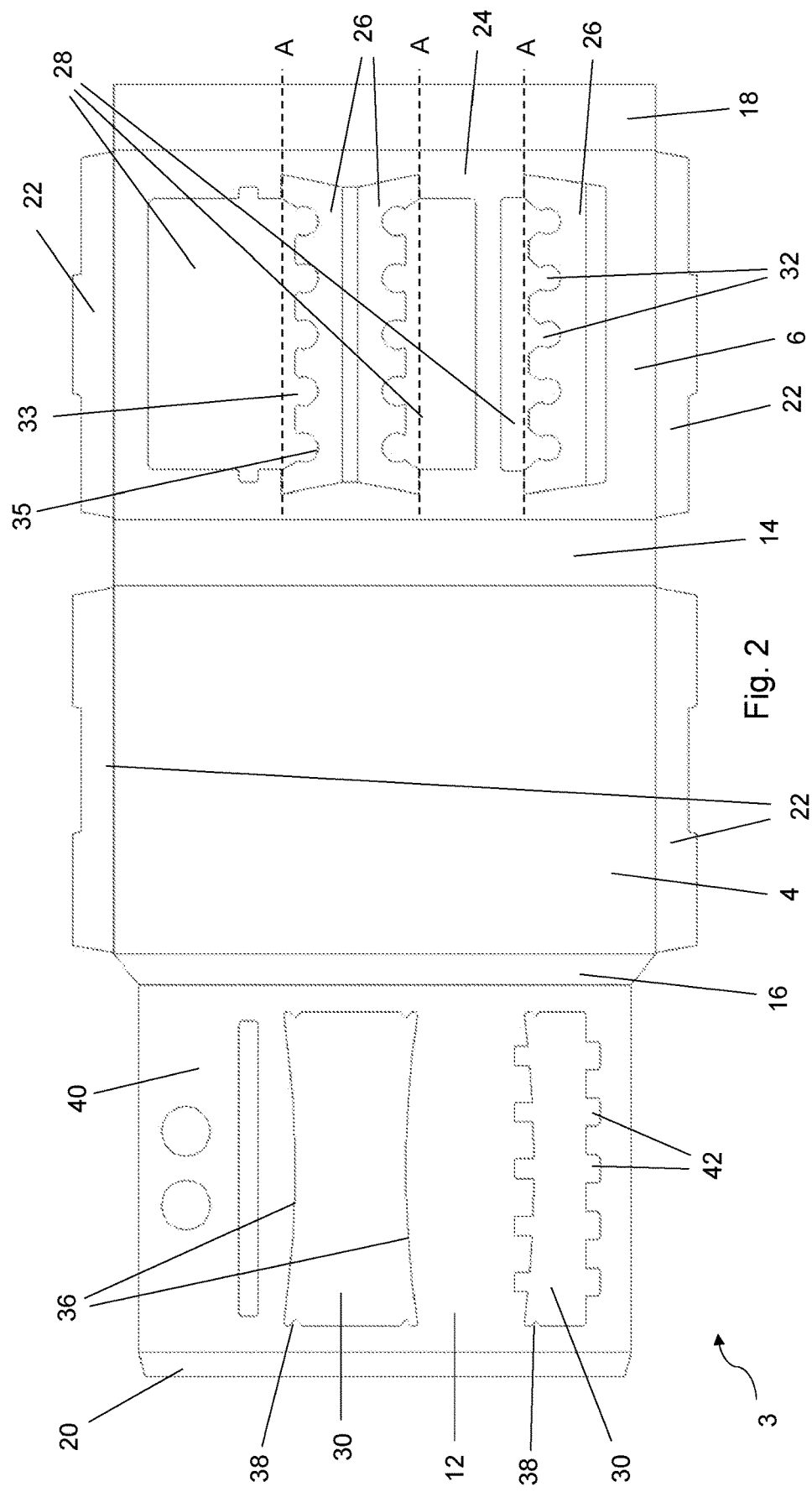
FIG. 2 is a plan view of an integral pack blank from which the pack in FIG. 1 can be formed.

The underlying integral pack blank 3 is illustrated in plan view in FIG. 2. In addition to the bottom layer 4 and the top layer 6, an intermediate layer 12 of the subsequent pack 2 can also be seen here. In the example illustrated, the bottom layer 4 is arranged between the top layer 6 and the intermediate layer 12 in the pack blank. The bottom layer 4 is connected to the top layer 6 by means of a first connecting strip 14. The bottom layer 4 is likewise connected to the intermediate layer 12 by means of a second connecting strip 16. A first side strip 18 is furthermore arranged on the side of the top layer 6 which faces away from the bottom layer 4, and a second side strip 20 is furthermore arranged on the side of the intermediate layer 12 which faces away from the bottom layer 4.

The connecting strips 14, 16 and the side strips 18, 20 are each connected pivotably to the associated layers 4, 6, 12. When the pack blank 3 is erected, the intermediate layer 12 is initially folded inwards over the bottom layer 4, and the top layer 6 is then folded over the two other layers 4, 12 by means of the connecting strip 14, and thus forms the upper boundary of the pack 2. Surfaces of the side strips 18, 20 and of the connecting strips 14, 16 which meet are each preferably adhesively bonded to one another.

As illustrated in FIG. 2, two mutually opposite closure tabs 22, which come to rest against the ends 10 of the pack 2 after the pack 2 has been erected, are furthermore arranged on the bottom layer 4 and the top layer 6. To produce the pack 2, the mutually opposite closure tabs 22 on each end 10 of the pack 2 must each be pivoted in opposite directions, and then latch into one another. As a result, the state of the pack 2 illustrated in FIG. 1 is obtained, this being referred to below as the initial state.

In the erected pack 2, there is therefore a sandwich of three layers: the bottom layer 4, the top layer 6 and the intermediate layer 12 situated between them. The three layers 4, 6, 12 are each spaced apart from one another.

The bottom layer 4 is preferably formed by a continuous closed layer.

Figure 3:
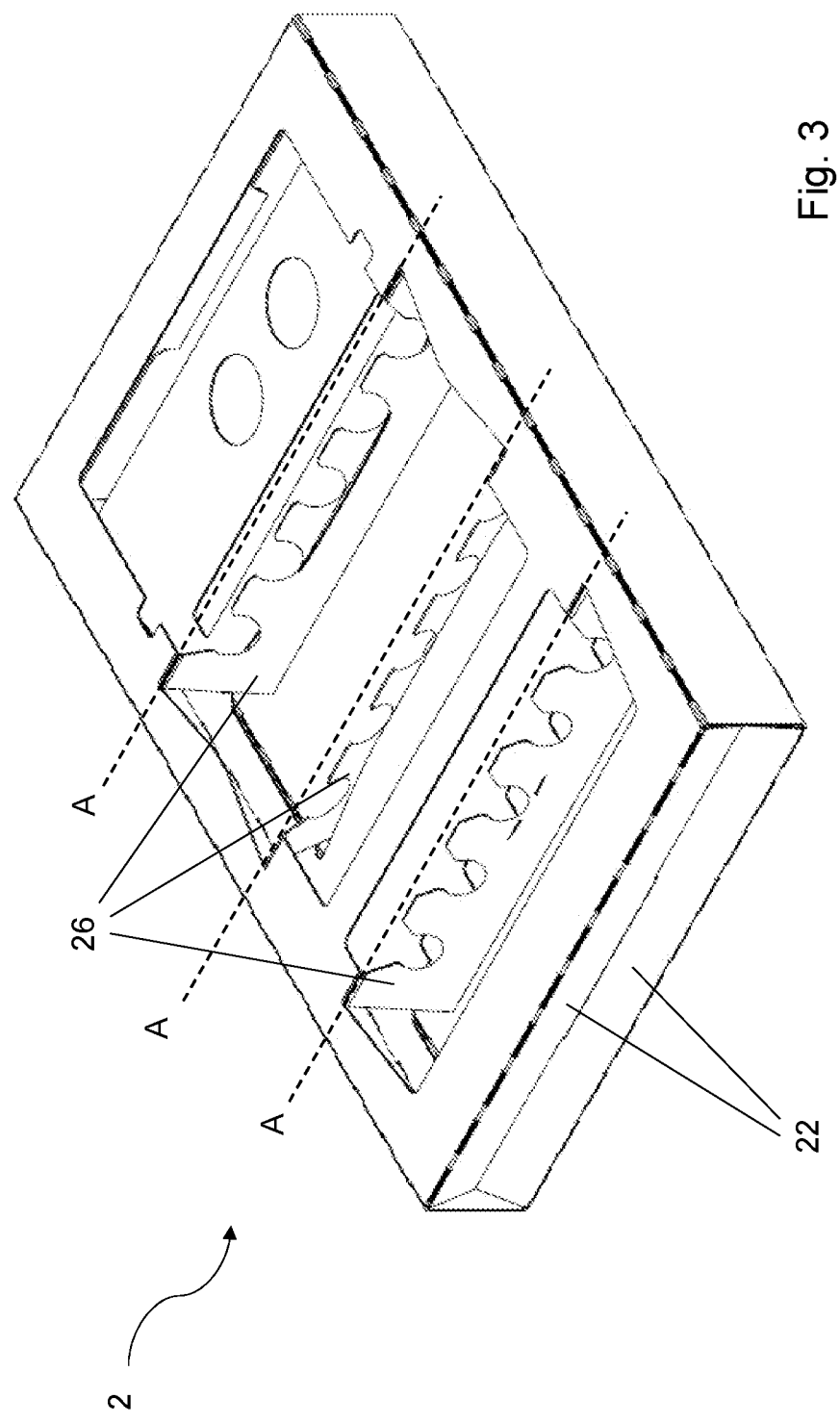
FIG. 3 is a perspective view of the pack in FIG. 1 in a pivoted receiving state of the receiving strips.

In the embodiment illustrated, the top layer 6 comprises a main body 24, which is formed by a plurality of interconnected webs, and three receiving strips 26. Two larger apertures 28, within which the receiving strips 26 are also situated, are provided between the webs of the main body 24. In the initial state of the pack 2, which is illustrated in FIG. 1, the receiving strips 26 extend substantially flat with respect to the main body 24 of the top layer 6. Each receiving strip 26 is connected pivotably to the main body 24 in two edge regions. The corresponding pivoting axes A are depicted in FIG. 1. Here, the two centrally arranged receiving strips 26 are pivotable in opposite directions. Each receiving strip 26 has a plurality of recesses 32 for supporting products 34 (see FIG. 4), wherein, in the pivoted receiving state (FIG. 3) of the receiving strip 26, entry openings 33 of the recesses 32 for the insertion of the products 34 point away from the bottom layer 4, and supporting sections 35 of the recesses 32 for supporting portions of the products 34 form a boundary of the recesses 32 which lies opposite the entry openings 33.

In the embodiment illustrated, the intermediate layer 12 comprises two apertures 30 in the pivoting region of the receiving strips 26, as is most clearly apparent from FIG. 2. Each aperture 30 comprises one or two edge contours 36, against each of which a downwardly pivoted receiving strip 26 comes to rest in the pivoted receiving state illustrated in FIG. 3. The edge contour 36 is in each case a convex contour or has mutually spaced sections which, when connected virtually, define a convex contour (FIG. 2). In each aperture 30 and close to the edge contour 36, the intermediate layer 12 furthermore has two symmetrically arranged latching lugs 38 for each downwardly pivoted receiving strip 26. Finally, the intermediate layer 12 has, offset from the receiving strips 26, supporting surfaces or supporting lines 40 for supporting additional product portions and/or has apertures 42 for receiving additional product portions.

Figure 6:
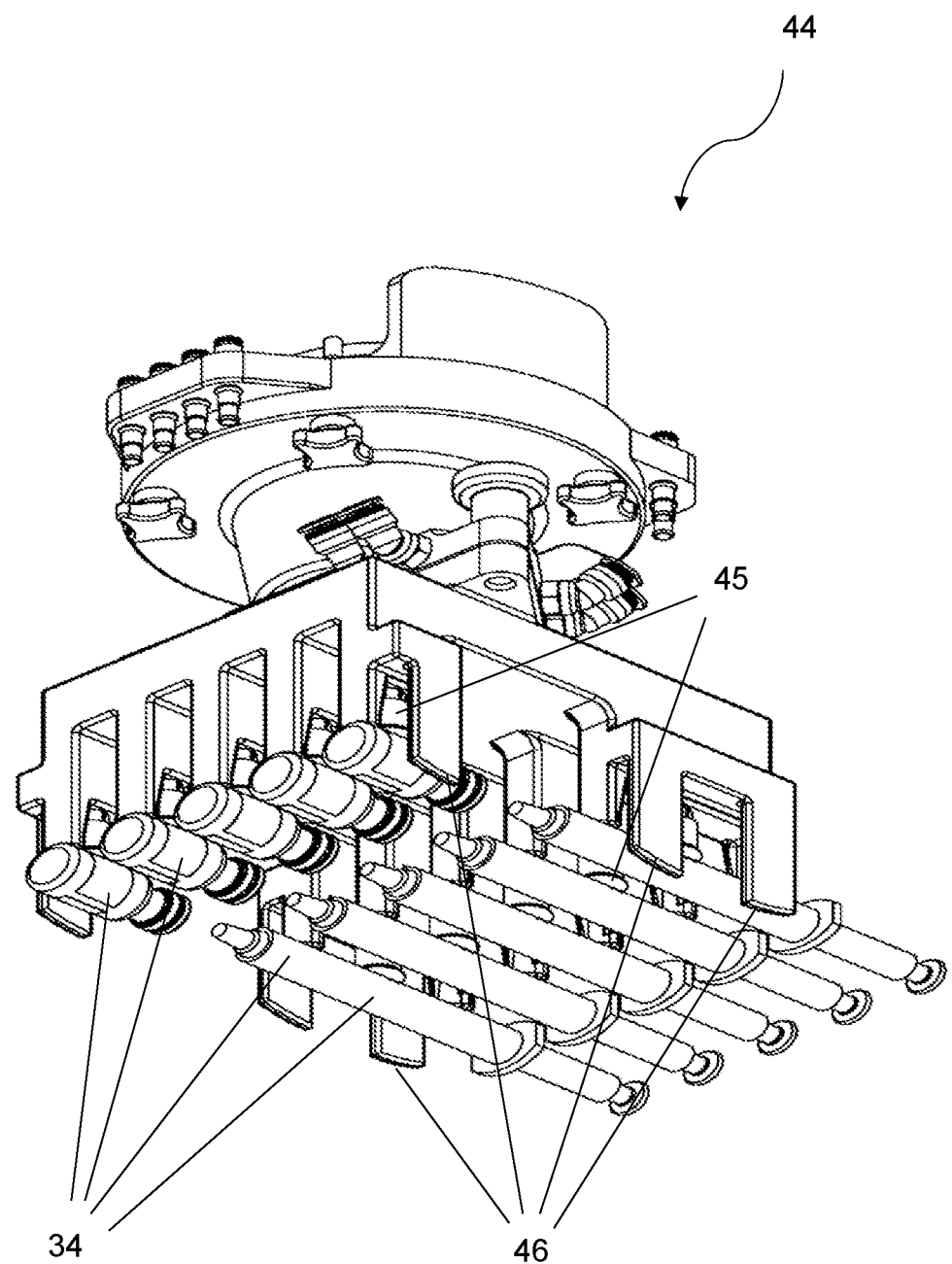
FIG. 6 is an enlarged plan view of an edge contour of the large aperture of the intermediate layer in FIG. 2.

In FIG. 6, an edge contour 36 is depicted on an enlarged scale. The height H of the convex contour at the vertex thereof, measured from the line of intersection S through the two end points 43 of the convex contour, is preferably between 1% and 10%, more preferably between 2 and 6%, of the width B of the convex contour between the two end points 43. The height H of the convex contour is in a range between 2 and 10 mm, for example.

Figure 4:
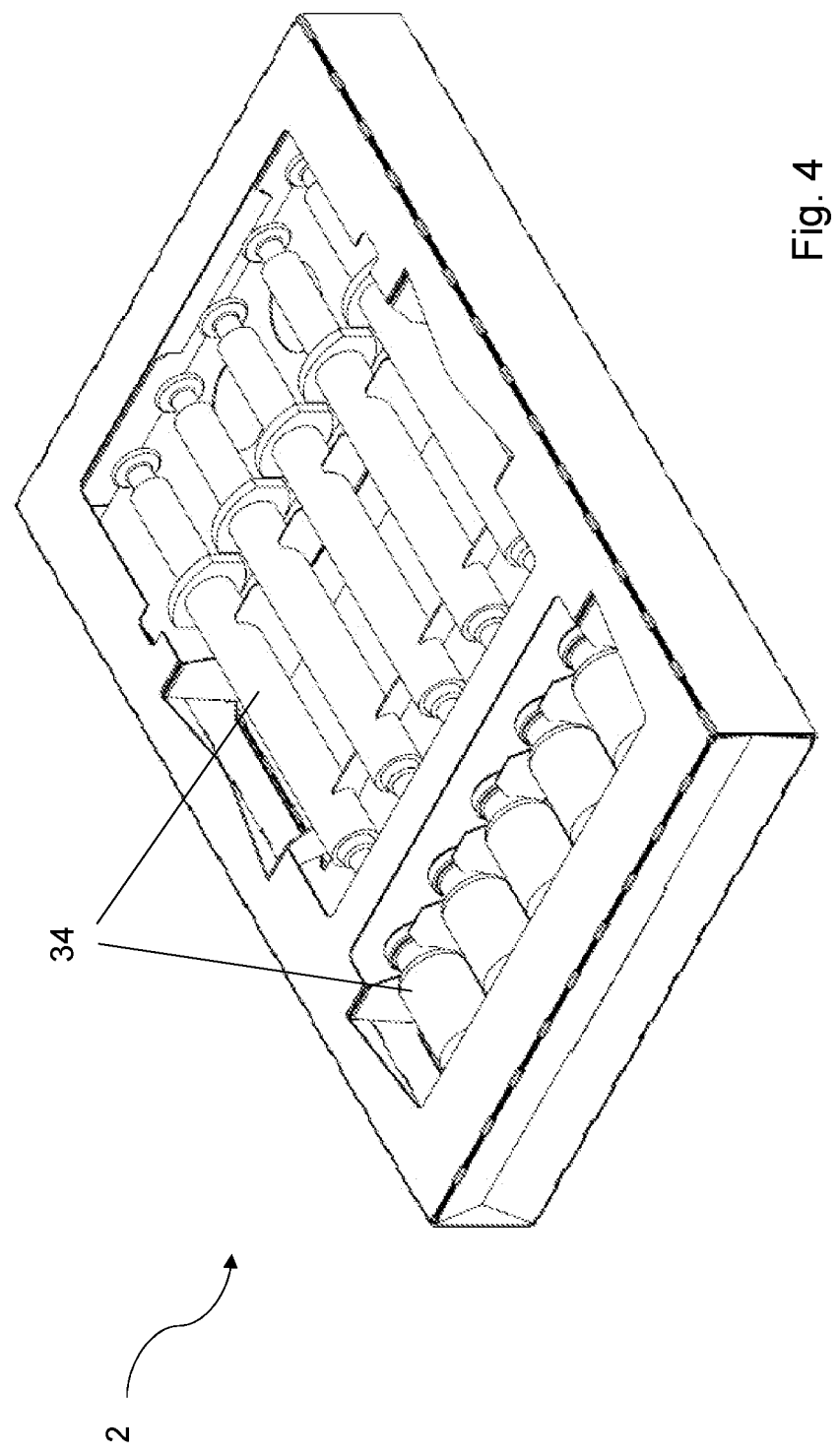
FIG. 4 is a perspective view of the pack according to FIG. 3, which is filled with products.

Finally, FIG. 4 illustrates a pack 2 filled with products 34. Here, the products 34 are resting in the recesses 32 of the receiving strips 26. In the example illustrated, the products 34 are vials and syringes, wherein the syringes are each supported on two receiving strips 26 on account of their length.

Figure 5:
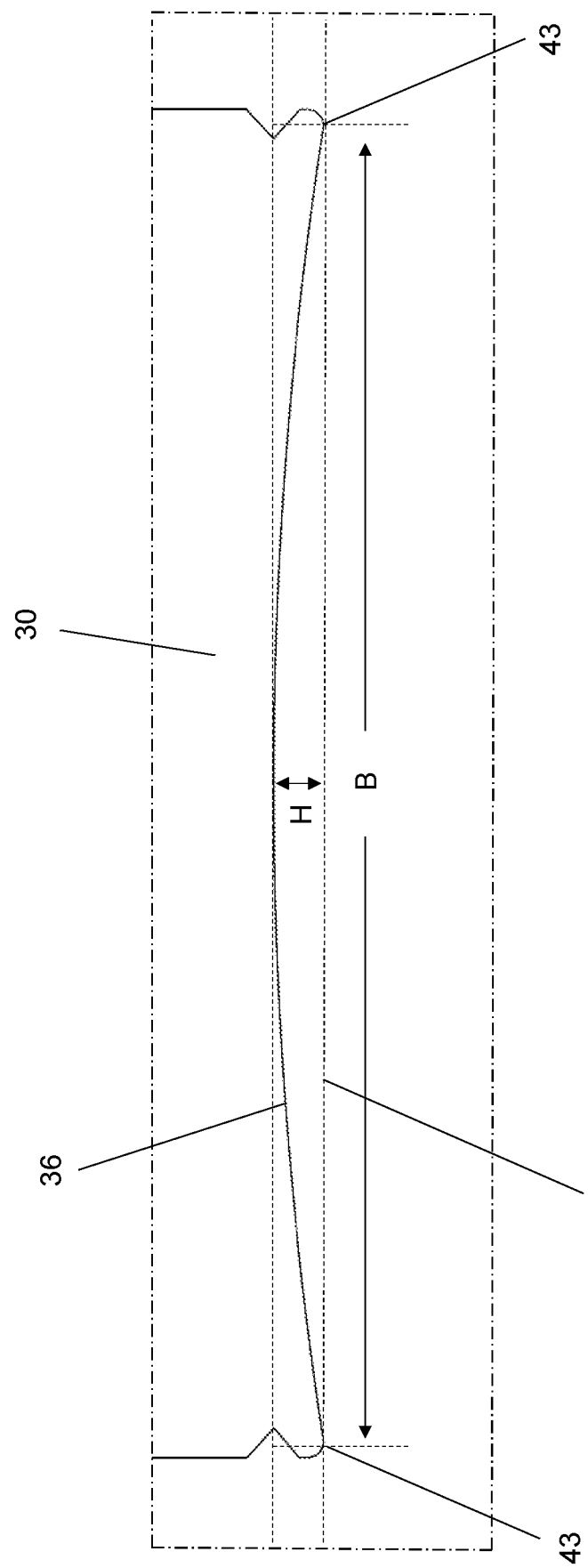
FIG. 5 is a perspective view from below of one embodiment of a filling device for the pack in FIG. 1.

The packs 2 are preferably filled with products 34 in an automated manner by means of a filling device 44 (illustrated by way of example in FIG. 5), which has suction devices or grippers 45 for the products 34 and performs a linear movement in the direction of the bottom layer 4.

By virtue of the linear movement, preferably by means of shoulders or projections 46 of the filling device 44, the receiving strips 26 are first of all pivoted in the direction of the bottom layer 4. After this or partially in overlap with respect to time, the linear movement simultaneously introduces a plurality of products 34 into the recesses 32 of the pivoted receiving strips 26.

After the filling process has taken place, the filling device 44 releases the products 34, and the filling device 44, which is then empty, can be moved back again in a direction away from the bottom layer 4 by a linear movement. Cyclical filling is preferred here. However, it is also conceivable to move the filling device 44 together with the moved pack 2 in a direction perpendicular to the direction of the linear movement.

Apart from the illustrated embodiment of the pack 2, many other embodiments are also conceivable. For example, the number of receiving strips 26 and the arrangement thereof and the pivoting direction can be varied in any desired manner.

The invention claimed is:

1. A pack for products, comprising:
   a bottom layer and a top layer, which are arranged one above the other and at a distance from one another and which are connected to one another,
   wherein the top layer comprises at least one receiving strip, which has a plurality of recesses,
   wherein the at least one receiving strip is pivotable in a direction of the bottom layer about at least one pivoting axis, which is arranged in a region of the top layer,
   wherein, in a pivoted receiving state of the at least one receiving strip, entry openings of the recesses for the insertion of the products point away from the bottom layer, and supporting sections of the recesses for supporting portions of the products form a boundary of the recesses which lies opposite the entry openings,
   wherein an intermediate layer is arranged between the bottom layer and the top layer, at a distance from the bottom layer and the top layer, and is connected to the bottom layer or to the top layer, wherein the intermediate layer has at least one aperture in a pivoting range of the at least one receiving strip.

2. The pack of claim 1, wherein the at least one aperture in the intermediate layer has at least one edge contour, which the at least one downwardly pivoted receiving strip abuts.

3. The pack of claim 2, wherein the at least one edge contour is a convex contour or has mutually spaced sections which, when connected virtually, define a convex contour.

4. The pack of claim 3, wherein a height of the convex contour at a vertex thereof, measured from a line of intersection through two end points of the convex contour, is between 1 and 10 mm.

5. The pack of claim 3, wherein the convex contour has a shape of a circular segment with a radius of curvature of between 25 and 2500 mm.

6. The pack of claim 1, wherein the intermediate layer has, in the at least one aperture and close to the edge contour, two symmetrically arranged latching lugs for the at least one downwardly pivoted receiving strip.

7. The pack of claim 1, wherein, in an unpivoted initial state, the at least one receiving strip and the recesses thereof extend substantially flat with respect to a remaining main body of the top layer or extend obliquely at an angle of no more than 30° relative to the main body of the top layer.

8. The pack of claim 1, wherein the pivoting axis is defined by at least one groove edge in the top layer.

9. The pack of claim 1, wherein the at least one receiving strip and a main body of the top layer are connected to one another in two opposite side regions of the top layer.

10. The pack of claim 1, wherein the top layer has two receiving strips, which are pivotable in opposite directions and the recesses of which serve to receive different portions of the same products.

11. The pack of claim 1, wherein the intermediate layer has, offset from the at least one receiving strip, supporting surfaces or supporting lines for supporting additional product portions or has apertures for receiving additional product portions.

* * * * *